United States Patent [19]
Wong

[11] Patent Number: 5,810,584
[45] Date of Patent: Sep. 22, 1998

[54] ORTHODONTIC APPLIANCES (BRACKETS) HAVING PRE-APPLIED ADHESIVE

[75] Inventor: Raymond F. Wong, Chino Hills, Calif.

[73] Assignee: Ormco Corporation, Glendora, Calif.

[21] Appl. No.: 833,080

[22] Filed: Apr. 4, 1997

[51] Int. Cl.⁶ ........................................ A61C 3/00
[52] U.S. Cl. ................................................ 433/9
[58] Field of Search ................................ 433/9; 206/635, 206/368

[56] References Cited

U.S. PATENT DOCUMENTS

| | | |
|---|---|---|
| 3,797,115 | 3/1974 | Silverman et al. . |
| 4,204,325 | 5/1980 | Kaelble ........................................ 433/9 |
| 4,948,367 | 8/1990 | Haas ............................................ 433/9 |
| 4,978,007 | 12/1990 | Jacobs et al. ............................ 206/469 |
| 5,015,180 | 5/1991 | Randklev ..................................... 433/9 |
| 5,172,809 | 12/1992 | Jacobs et al. ............................ 206/368 |
| 5,183,403 | 2/1993 | Masuhara et al. ........................... 433/9 |
| 5,219,283 | 6/1993 | Farzin-Nia et al. ......................... 433/9 |
| 5,221,202 | 6/1993 | James ........................................... 433/9 |
| 5,354,199 | 10/1994 | Jacobs et al. ............................... 433/9 |
| 5,429,229 | 7/1995 | Chester et al. .............................. 433/9 |
| 5,538,129 | 7/1996 | Chester et al. ......................... 206/63.5 |
| 5,552,177 | 9/1996 | Jacobs et al. ........................... 427/2.29 |
| 5,575,645 | 11/1996 | Jacobs et al. ............................... 433/9 |

OTHER PUBLICATIONS

Adhesive Precoated Brackets Instructions, 3M Unitek, 1992.
One Adhesive . . . Many Options, American Orthodontics.
Shear Strength of APC Brackets Bonded to Extracted Teeth: A Pilot Study, B. M. Oliver et al., pp. 1–12.

Indirect Bonding with Adhesive Precoated Brackets, R. B. Cooper et al., JCO/Mar. 1993, vol. XXVII, No. 3, pp. 164–167.

Update on Bonding Brackets: An In Vitro Survey, G. V. Newman et al., JCO/Jul. 1994, vol. XXVIII, No. 7, pp. 396–402.

*Primary Examiner*—Cary E. O'Connor
*Attorney, Agent, or Firm*—Wood, Herron & Evans, L.L.P.

[57] ABSTRACT

Orthodontic appliances (brackets) having a pre-applied or factory applied adhesive thereon presenting a non-tacky surface are described. The brackets, which may be plastic, metal or ceramic, have a bonding base surface to which an appropriate adhesive composition is pre-applied. The adhesive, which is uncured and generally presents a tacky outer surface, is protected from deterioration or disturbance by the attachment or adherence of particles, which may form a layer, on the outer surface of the adhesive, thereby presenting a non-tacky surface. Also included are articles consisting of a container with a cover and an orthodontic bracket having pre-applied adhesive received in the container. The adhesive on the bracket in the container presents a non-tacky surface by virtue of a layer of particles secured to the otherwise tacky adhesive surface.

30 Claims, No Drawings

ORTHODONTIC APPLIANCES (BRACKETS) HAVING PRE-APPLIED ADHESIVE

FIELD OF THE INVENTION

The invention relates to orthodontic appliances (brackets) having pre-applied adhesive and to methods of adhering orthodontic brackets to tooth surfaces.

BACKGROUND OF THE INVENTION

In the field of orthodontics, it has become increasingly important to enhance the bonding strengths achieved when adhering orthodontic appliances, particularly brackets, to patient's teeth. A competing concern, however, is the reduction of the cost of installing a set of brackets on a patient's teeth by reducing the amount of chair-side time spent by the orthodontist. One technique that has become increasingly popular is the use of pre-applied adhesives or factory-applied adhesives on the bonding surface of the orthodontic appliance or bracket. For example, U.S. Pat. Nos. 4,978,007; 5,172,809; 5,015,180; 5,328,363; 5,429,229; 5,183,403; 5,221,202; 4,948,367; 4,204,325; 5,575,645; 5,538,129; 5,552,177; 3,797,115; and 5,354,199 all relate to orthodontic brackets having pre-applied adhesive thereon.

By shipping orthodontic brackets with the adhesive already applied thereto, the clinician is saved the time normally spent in preparing the adhesive and applying it to the bracket. This serves to reduce the overall cost of the procedure of applying a set of brackets to a patient's teeth, and it also serves to enhance the consistency of the adhesive bonds achieved when the brackets are applied to the patient's teeth. This latter point can be critically important since inconsistent bonding strengths between the various brackets on a patient's teeth may result in debonding of one or more brackets during the treatment process. Factory-applied adhesives typically have more consistent compositional characteristics, thus resulting in more consistent adhesive bonding.

One drawback associated with factory-applied adhesives is the limitation on how such brackets are packaged and shipped. It is important that the adhesive layer pre-applied to the bracket bonding surface not be disturbed or degraded at any time prior to application to the patient's tooth. This can present a number of problems since typically the adhesive surface is tacky. Disturbance or deterioration of the adhesive layer is undesirable as it may diminish the bonding capacity of the adhesive and/or cause inconsistent bonding properties. One technique that has been employed to attempt to protect the adhesive surface is a release layer or release tape covering the otherwise exposed adhesive surface on the bracket. When ready for use, the release tape is pulled away from the bracket, or vice versa. One drawback to such arrangements is that at least a portion of the adhesive may be removed with the tape, thereby deleteriously affecting the bonding integrity of the bracket.

Therefore, what is needed is an orthodontic bracket having a factory-applied adhesive in which the adhesive surface is protected in such a manner that the adhesive surface is not disturbed or degraded, and wherein the bond strengths achieved using the brackets with factory-applied adhesive are enhanced.

SUMMARY OF THE INVENTION

In its broadest aspects, the present invention is directed to improvements in orthodontic appliances (brackets) wherein a pre-applied or factory-applied adhesive thereon presents a non-tacky surface. The invention also relates to methods of adhering orthodontic brackets with pre-applied adhesive to tooth surfaces. The appliances of the present invention are advantageous in that they can be shipped without the typical concern for suspending or otherwise keeping the pre-applied adhesive from contacting the container. This is because in the instant invention, the outer surface layer of the adhesive is non-tacky. Furthermore, the present invention obviates the use of release tapes and other such means for attempting to protect the adhesive surface.

More specifically, orthodontic brackets, which may be plastic, metal or ceramic, have a bonding base surface to which an appropriate adhesive composition is pre-applied by the manufacturer. The adhesive, which is uncured, generally presents a tacky outer surface. The means of protecting that tacky surface from deterioration, degradation or disturbance in the present invention is the attachment, adherence or partial embedding of particles, which may form a layer, to the outer surface of the adhesive. The particles, which may be any one or combination of different materials, including inorganic or organic particles, are secured to the exposed adhesive surface. Upon application of the particles, the surface presented is non-tacky and therefore not readily subjected to deterioration or disturbance by delamination, as would normally occur upon disturbance of a typical tacky adhesive, such as when release tapes or layers are utilized.

In a preferred embodiment, an orthodontic bracket having pre-applied adhesive of the present invention is a metal bracket having a mesh bonding surface on the base thereof. The bracket has a first adhesive coating applied onto the bonding mesh and that first adhesive coating is pre-cured. Thereafter, a second adhesive layer is applied which remains uncured. It is preferable that this second adhesive have long-term shelf stability characteristics in the uncured state. The particles are then applied by either dipping or sprinkling. By way of example, but not limitation, the particles may be made of an inorganic material such as barium alumino borosilicate, quartz, or soda lime glass. Alternatively, the particles may be a synthetic organic polymer such as methylmethacrylate, ethylmethacrylate, or methyl/ethyl copolymers. Regardless of the particular material of the particles, those particles are secured to the outermost portion of the adhesive layer. In one embodiment, the particles are partially embedded in the adhesive. The particles ultimately become an integral part of the adhesive upon application of the bracket to a tooth, but since they may be only partially embedded at the time of application, there is presented a non-tacky outer surface. It is believed that the combination of a pre-cured adhesive layer and an uncured adhesive layer result in improved bond strength.

Turning to application of the brackets of the present invention, it is desirable that a tacky surface be created at chair side to aid in application of the brackets to a patient's teeth. Achieving the desired tackiness may be dependent upon the adhesive consistency as well as the tooth primer (sealant). In particular, the primer should wet the particles effectively to allow the adhesive-particles-primer mixture to immediately become tacky when the bracket is placed; otherwise, the bracket may experience excessive drift or completely fall off the tooth when the bracket placement instrument is withdrawn. Upon application of the appropriate tooth primer and adherence of the bracket to the tooth, curing is effected by visible light radiation, as is well known in the art.

These and other features and advantages of the present invention will become apparent to persons skilled in the art upon review of the detailed description and examples hereinbelow.

DETAILED DESCRIPTION OF THE INVENTION

The present invention is directed to orthodontic appliances, and particularly orthodontic brackets, which have an adhesive applied to the bonding surface thereof, wherein the adhesive has a non-tacky surface. In one preferred embodiment, the adhesive includes two distinct visible light-curable pastes and the non-tacky surface is the result of a layer of synthetic organic polymer particles partially embedded within the exposed adhesive surface.

In one aspect of the present invention, the brackets are metal brackets which have a mesh bonding base. In this context, bond failure predominantly occurs at the mesh-adhesive interface because, during adhesive curing, the light is unable to fully penetrate the most shadowed area (i.e., the mesh interstices). As a means of addressing this problem, it is contemplated in the present invention that a first adhesive composition is applied to the bonding surface and mesh. This adhesive is worked into the mesh and then smeared level to the mesh surface using a spatula. This adhesive is cured using a Demetron 400 visible light curing light or equivalent (output of at least 300 mw/cm$^2$) at a distance of 5 mm or less, directly perpendicular to the mesh surface for approximately 10 seconds. This first adhesive composition will hereinafter be referred to as Paste A. Pre-curing of Paste A yields a maximum monomer to polymer conversion allowing full bonding strength to develop within the mesh area. One contemplated composition for Paste A that provides suitable results is the Sequence™ adhesive available from Ormco Corporation, Glendora, Calif. (Part No. 740-0148). The composition of Sequence is as follows:

| Component | Weight Percent |
| --- | --- |
| camphorquinone | 0.20% |
| barium aluminum borosilicate | 71.97% |
| hydroxy ethyl methacrylate | 6.13% |
| benzoyl peroxide | 0.30% |
| titanium dioxide | 0.04% |
| mercaptobenzothiazole | 0.30% |
| ethoxylated bisphenol A dimethacrylate | 10.13% |
| diethylaminoethylmethacrylate-BF$_3$ | 0.80% |
| Sybron ATPU | 10.13% |

It will be appreciated that a variety of adhesives may be suitable substitutes for the above-described Paste A; however, the choice of composition will result in variations of ultimate bond strength. The reason for this is that different adhesives possess differing abilities to couple with the stainless steel mesh (wetting characteristics, chemical affinity, etc.), the strength of the adhesive material (this is a mechanical bond that requires reinforced anchoring of adhesive tangs), and the ability of Paste A to couple with the Paste B adhesive discussed below. Finally, it should be noted that utilizing a pre-cured Paste A may not be necessary at all for brackets, particularly clear brackets, or other bonding base configurations that do not utilize a metallic mesh.

The present invention further contemplates a second adhesive dispensed directly onto the mesh bonding pad. This second adhesive formulation will be referred to hereinafter as Paste B. Preferably, Paste B is a shelf-stable, high viscosity paste which is capable of maintaining its handling, curing and aesthetic characteristics while on a bracket in a package for at least one year at room temperature. It is contemplated that Paste B is dispensed directly onto the mesh bonding base of a metal bracket which has the pre-cured Paste A thereon. The consistency of the material may be such that Paste B is not self-leveling when applied to the bracket, in which case it may require teasing to form a desired geometry. It will be appreciated that as an alternative, Paste A may not be used at all and Paste B is the sole adhesive. Furthermore, although bond strength is found to be higher when a pre-cured Paste A is present within the mesh bonding surface, it is contemplated that the Paste B would be utilized by itself even on metal brackets having mesh bonding surfaces.

One preferred Paste B composition which has demonstrated satisfactory results is as follows:

| Component | Weight Percent |
| --- | --- |
| camphorquinone | 0.03% |
| ethyl-4-(dimethylamino)benzoate | 0.12% |
| barium aluminum borosilicate | 69.83% |
| ethoxylated bisphenol A dimethacrylate | 15.01% |
| Bis GMA | 15.01% |
| 2,6-di-t-butyl-4-methylphenol | 0.003% |

The above formulation can be modified through filler selection if different handling characteristics are required. Ideally, paste dispensing onto the bracket should be automated and therefore the flow characteristics may require adjustment.

An alternative Paste B composition contemplated for use in the present invention has the following composition:

| Component | Weight Percent |
| --- | --- |
| camphorquinone | 0.03% |
| ethyl-4-(dimethylamino)benzoate | 0.12% |
| barium aluminum borosilicate | 62.50% |
| silica | 6.25% |
| ethoxylated bisphenol A dimethacrylate | 21.80% |
| trimethylopropane trimethacrylate | 9.30% |
| 2,6-di-t-butyl-4-methylphenol | 0.003% |

The above formulation may provide improved stability vis-a-vis the first described Paste B formulation.

Yet another contemplated alternative Paste B has the following composition:

| Component | Weight Percent |
| --- | --- |
| camphorquinone | 0.3% |
| ethyl-4-(dimethylamino)benzoate | 0.12% |
| barium aluminum borosilicate | 63.8% |
| silica | 5.3% |
| Bis GMA | 20.60% |
| trimethylopropane trimethacrylate | 10.15% |
| 2,6-di-t-butyl-4-methylphenol | 0.003% |

Subsequent to application of the adhesive to the bonding surface of the bracket, a non-tacky exposed surface is provided by applying a layer or coating of particles to the exposed adhesive surface. In a preferred embodiment of the invention, the particles, which may be spherical or any other suitable shape, become partially embedded in the outermost portion of the Paste B adhesive. The particles form an integral part of the adhesive; however, the exposed surfaces of the particles are free of monomeric resin, thereby rendering a dry, plastic-like, non-tacky exposed surface. One suitable type of particles are commercially available Polymer 82™, available from Sybron Chemicals. Polymer 82™ is a 50/50 copolymer of poly(ethyl/methylmethacrylate) with a trace of a peroxide initiator. The particles are solid, plastic spheres, non-agglomerating, individual and free-flowing. The size range is approximately 0.001 to 0.0005" in diameter. The bracket assembly having Paste B thereon is dipped into Polymer 82™ powder, or the powder is sprinkled onto the exposed Paste B. The paste will only accept a layer or coating because the small mass of a sphere immediately sticks to any exposed resinous surface, and when all spaces are occupied, excess spheres freely flow over the non-tacky surface, unable to attach.

As an alternative to the Polymer 82™ particles, another product, Polymer 65CLC (also available from Sybron Chemicals) provides good results. Polymer 65CLC is approximately 95% polymethylmethacrylate and 5% diacrylate cross-linker. The polymer spheres have a diameter size range of about sit 3 to 100 microns. The particle layer or coating may also comprise solid soda lime glass spheres, such as are available from Potters Industries under the designation Product 3000CP-01. These glass spheres are believed to have a diameter in the range of 5–45 microns.

In use and application, the brackets of the present invention having an adhesive composition and a layer or coating of particles to present a non-tacky surface, are applied to a tooth surface which has been treated with a primer (sealant). Generally speaking, the primer should be hydrophilic. The primer essentially becomes the coupling agent for attaching the non-tacky surface of the Paste B adhesive to a porous, slightly moist tooth enamel. The primer should be light curable and shelf stable in conventional packaging. One contemplated primer composition is as follows:

| Component | Weight Percent |
|---|---|
| camphorquinone | 0.10% |
| ethyl-4-(dimethylamino)benzoate | 0.42% |
| hydroxy ethyl methacrylate | 26.5% |
| Bis GMA | 73.0% |
| 2,6-di-t-butyl-4-methylphenol | 0.01% |

The above primer, which is a low viscosity, clear liquid, is painted onto dry, etched enamel. The bracket of the present invention with a non-tacky pre-applied adhesive is then positioned on the primed tooth and a light cure affixes the appliance. It is believed that the mechanism involved includes pressing the particles into the adhesive and there is presented an intermixed zone wherein the adhesive and the primer are intermixed at their interface. At that intermixed zone, the particles become scattered or dispersed in the adhesive/primer intermix. Upon light curing utilizing well known light curing techniques, the adhesive and primer are copolymerized into a cross-linked network or matrix that encompasses the particles.

While the invention has been described in particularity and with reference to specific examples, the invention is not intended to be limited to such particulars. It will be appreciated by persons skilled in the art that various modifications can be made to the invention without departing from the scope thereof as defined in the appended claims.

What is claimed is:

1. An orthodontic bracket having pre-applied adhesive, comprising:
   a bracket having a bonding base;
   an adhesive composition applied to said bonding base and presenting a tacky surface; and
   a layer of particles secured to said tacky surface of said adhesive composition, thereby presenting a substantially non-tacky surface.

2. The orthodontic bracket of claim 1 wherein said bracket is made of a material selected from the group consisting of metal, plastic and ceramic.

3. The orthodontic bracket of claim 2 wherein said bracket is metal.

4. The orthodontic bracket of claim 3, further comprising a bonding mesh attached to said bonding base.

5. The orthodontic bracket of claim 1 wherein said adhesive composition has a substantially long-term shelf life in an uncured state.

6. The orthodontic bracket of claim 1 wherein said particles are made of an inorganic material selected from the group consisting of barium alumino borosilicate, quartz, and soda lime glass.

7. The orthodontic bracket of claim 1 wherein said particles are made of a material selected from the group consisting of synthetic organic polymers.

8. The orthodontic bracket of claim 7 wherein said synthetic organic polymer is selected from the group consisting of methylmethacrylate, ethylmethacrylate, and methyl/ethyl copolymers.

9. The orthodontic bracket of claim 1 wherein said adhesive includes Bis GMA.

10. The orthodontic bracket of claim 1 wherein said adhesive includes EBADMA.

11. The orthodontic bracket of claim 1 wherein said adhesive includes Bis OMA and EBADMA.

12. The orthodontic bracket of claim 1 wherein said adhesive includes TMPTMA.

13. The orthodontic bracket of claim 1 wherein said adhesive includes TMPTMA and BisGMA.

14. The orthodontic bracket of claim 1 wherein said adhesive includes TMPTMA and EBADMA.

15. An orthodontic bracket having pre-applied adhesive, comprising:
   a bracket having a bonding base;
   a first adhesive composition applied to said bonding base;
   a second adhesive composition applied over said first adhesive composition and presenting a tacky surface; and
   a layer of particles secured to said tacky surface of said second adhesive composition, thereby presenting a substantially non-tacky surface.

16. The orthodontic bracket of claim 15 wherein said bracket is made of a material selected from the group consisting of metal, plastic and ceramic.

17. The orthodontic bracket of claim 16 wherein said bracket is metal.

18. The orthodontic bracket of claim 17, further comprising a bonding mesh attached to said bonding base and wherein said first adhesive composition at least partially envelopes said mesh.

19. The orthodontic bracket of claim 15 wherein said first adhesive composition is pre-cured.

20. The orthodontic bracket of claim 15 wherein said second adhesive composition differs from said first adhesive composition.

21. The orthodontic bracket of claim 15 wherein said second adhesive composition has a substantially long-term shelf life in an uncured state.

22. The orthodontic bracket of claim 15 wherein said particles are made of an inorganic material selected from the group consisting of barium alumino borosilicate, quartz, and soda lime glass.

23. The orthodontic bracket of claim 15 wherein said particles are made of a material selected from the group consisting of synthetic organic polymers.

24. The orthodontic bracket of claim 15 wherein said second adhesive include Bis GMA.

25. The orthodontic bracket of claim 15 wherein said second adhesive includes EBADMA.

26. The orthodontic bracket of claim 15 wherein said second adhesive includes Bis GMA and EBADMA.

27. The orthodontic bracket of claim 15 wherein said second adhesive includes TMPTMA.

28. The orthodontic bracket of claim 15 wherein said second adhesive includes TMPTMA and BisGMA.

29. The orthodontic bracket of claim 15 wherein said second adhesive includes TMPTMA and EBADMA.

30. An article, comprising:
   a container with a cover, and
   an orthodontic bracket having pre-applied adhesive received in said container, said bracket
   having a bonding base,
   an adhesive composition applied to said bonding base and presenting a tacky surface, and
   a layer of particles secured to said tacky surface of said adhesive composition, thereby presenting a substantially non-tacky surface.

* * * * *